United States Patent [19]

Rechnitz et al.

[11] 4,402,819
[45] Sep. 6, 1983

[54] ANTIBODY-SELECTIVE MEMBRANE ELECTRODES

[75] Inventors: Garry A. Rechnitz; Robert L. Solsky, both of Newark, Del.

[73] Assignee: University of Delaware, Newark, Del.

[21] Appl. No.: 313,587

[22] Filed: Oct. 21, 1981

Related U.S. Application Data

[63] Continuation of Ser. No. 131,384, Mar. 17, 1980, abandoned.

[51] Int. Cl.³ .......................................... G01N 27/46
[52] U.S. Cl. .................................... 204/418; 204/403
[58] Field of Search ............. 204/1 T, 195 R, 195 M, 204/195 L, 195 B, 418, 403

[56] References Cited

U.S. PATENT DOCUMENTS

| | | | |
|---|---|---|---|
| 3,966,580 | 6/1976 | Janata et al. | 204/195 B |
| 4,081,334 | 3/1978 | Suzuki et al. | 204/1 T |
| 4,151,049 | 4/1979 | Janata | 204/195 M |
| 4,214,968 | 7/1980 | Battaglia et al. | 204/195 M |
| 4,233,144 | 11/1980 | Pace et al. | 204/195 M |
| 4,276,141 | 6/1981 | Hawkins | 204/1 T |

OTHER PUBLICATIONS

"Science", 153, 185–188 (1966).
"J. Am. Chem. Soc."., 97, p. 2914–2915, (May 14, 1975).
Aizawa et al., "J. Membrane Science", 2, p. 125–132, (1977).
Yamamoto et al., "Chemical Letters", 3, p. 245–246, (1978).

*Primary Examiner*—T. Tung

[57] ABSTRACT

An antibody-selective potentiometric electrode for the quantitative determination of antibodies in dilute liquid serum samples employing an insoluble membrane incorporating an antigen having bonded thereto an ion carrier effecting the permeability of preselected cations therein, which permeability is a function of specific antibody concentrations in analysis, and the corresponding method of analysis.

8 Claims, 3 Drawing Figures

ANTIBODY-SELECTIVE MEMBRANE ELECTRODES

GENERAL

The research culminating in this invention was conducted under National Institutes of Health Grant No. GM25308, pursuant to which the Government possesses certain property rights.

This is a continuation of application Ser. No. 131,384 filed Mar. 17, 1980 now abandoned.

BACKGROUND OF THE INVENTION

As reported in *Science* 153, 185 (1966), *Am. Chem. Soc.* 97, 2914 (1975) E, *J. Membr. Sci.* 2, 125 (1977) and *Chemical Letters* p. 245 (1978 ) E, I, efforts to develop electrochemical probes have not been successful as regards practical sensors for antibodies.

SUMMARY OF THE INVENTION

This invention comprises an antibody selective potentiometric electrode for the quantitative determination of antibodies in a dilute liquid serum sample comprising, in an analytical electrode, a liquid-insoluble membrane incorporating an antigen having bonded thereto an ion carrier effecting the permeability of preselected cations in said membrane, said cation permeability being a function of specific antibody concentrations in analysis, interferants in the serum sample being substantially barred, and the corresponding method of analysis.

DRAWINGS

The following drawings constitute part of this disclosure, in which:

FIG. 1 is a schematic longitudinal cross-sectional view of the electrode tip region of a preferred embodiment of this invention, FIG. 2 is a plot of electrode response in millivolts on the ordinate versus antibody concentration (μg/ml) to dinitrophenol and to bovine serum albumin, respectively, on the abscissa and FIG. 3 is a plot of electrode response in millivolts on the ordinate versus antibody concentration (μg/ml to bovine serum albumin (untreated and absorbed, respectively) on the abscissa.

DETAILED DESCRIPTION OF THE INVENTION

Figure 1:
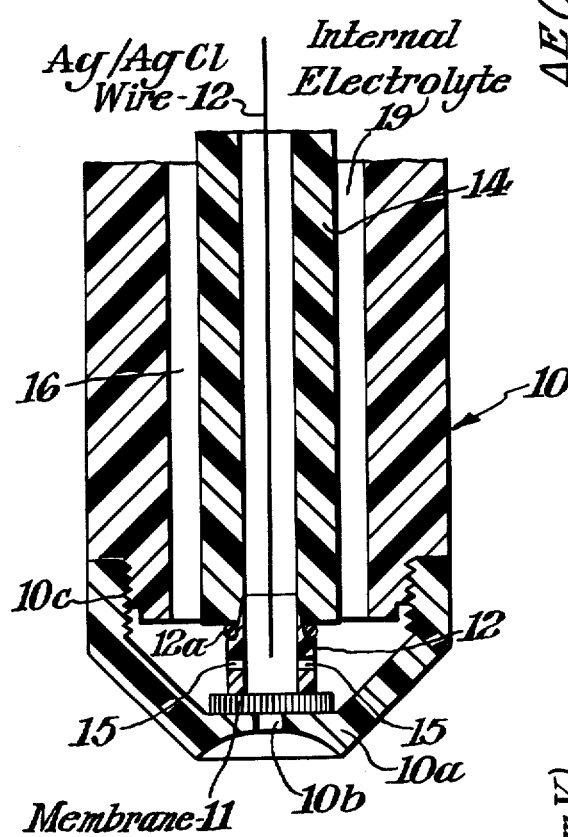

Referring to FIG. 1, there is shown in longitudinal cross-section the body of a commercially available Orion Research Co. 92 Series electrode customarily used to analyze for cations or anions in electrolytes, indicated generally at 10, provided, according to this invention, with an exchangeable, tip-mounted liquid-insoluble antibody sensing membrane disk 11 (typically, 4 mm. dia.×0.2 mm. thick).

Conveniently, membrane disk 11 can be mounted on the outboard end of polymeric nipple 12, which is friction-fitted (e.g., by a rubber O-ring seal 12a) to the open lower end of the inner barrel 14 of the electrode. Nipple 12 is drilled radially at 15 to communicate with the annular open space 16 of the electrode. The assembly is closed off by threaded cap 10a, axially drilled through at 10b, thereby establishing open communication with membrane disk 11, and the cap is attached to electrode body 10 by external threads 10c.

The commercial model of electrode 10 is filled with a 0.01 M aqueous NaCl electrolyte, which passes freely via ports 15, so that annular space 16 is also filled therewith.

(A) Introductory Details

As defined, an antigen is any substance which, when introduced into an animal biological system, will cause the formation of antibodies. Antigens have relatively high molecular weights of over 1000. A hapten is a lower molecular weight substance (e.g., below 1000 molecular weight) which, although it does not cause antibody generation upon introduction into an animal system, can be considered to be an antigen for the purposes of this invention because it behaves like an antigen when incorporated into the sensing membranes of this invention.

The potentiometrically effective entity of this invention is a membrane incorporating a preselected antigen having bonded thereto an ion carrier effecting the permeability of preselected cations (specifically, $K^+$, $Na^+$, $Ca^{++}$ and $Mg^{++}$) in the membrane.

The specific ion carrier utilized in the experiments hereinafter described was dibenzo-18-crown-6, hereinafter abbreviated DB-18-C-6, which has the structural formula

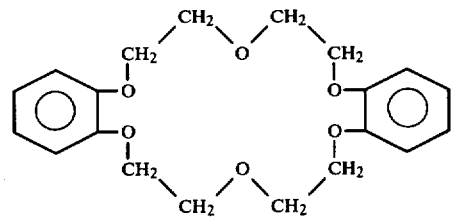

which is hereinafter schematically simplified to the following, wherein "E" represents the essentially inert central ether structure joining the symmetrically disposed benzene reactive members:

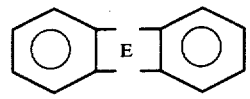

It is postulated that DB-18-C-6 sequesters preferentially $K^+$ or $Na^+$ in the cavity formed by the ether ring E.

(B) Preparation of the Antigen-Carrier Conjugates (1) The Dinitrophenyl Group-Carrier Conjugate In this instance, the antigen was the hapten dinitrophenyl (DNP) group and the reaction sequence was as follows:

(a) Nitration

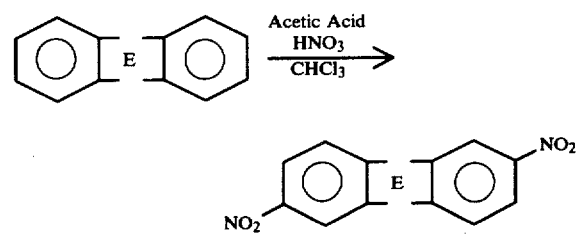

The product obtained was a mixture of cis-trans isomers, of which the trans was isolated for use by standard techniques.

(b) Standard Reduction

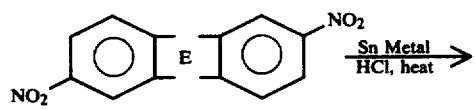

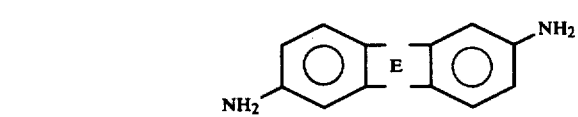

(c) Sanger Reaction

The dinitrophenyl group was introduced via the fluoride.

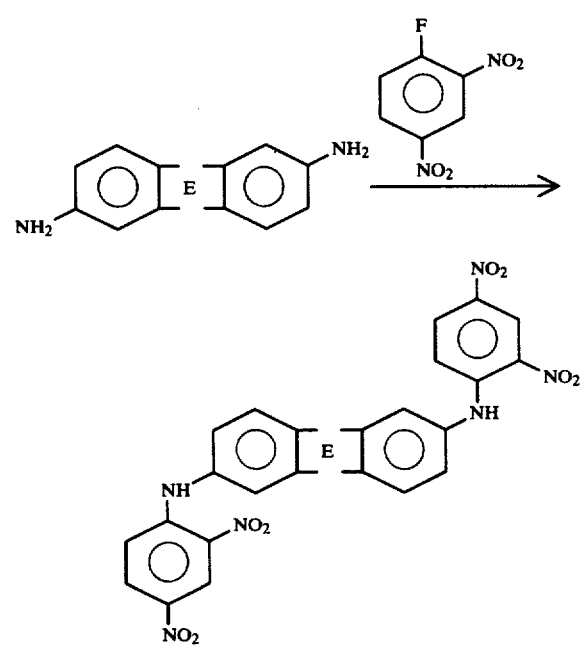

(2) The Bovine Serum Albumin Antigen-Carrier Conjugate

In this case, the entire antigen protein, bovine serum albumin (BSA), was coupled to the carrier. The BSA molecule possesses a minimum of six different antigenic determinants, as compared with the DNP case supra.

The antibody to BSA, as purchased, is a mixture of all the antibody molecules which can react with BSA. They may be directed toward different parts of the BSA molecule, but they are still the antibodies which do react with BSA and thus are unique from other populations of antibodies [refer *Journal of Biological Chemistry*, Vol. 253 (22), pp. 8087–8092 (1978)].

Using the same convention as in (B) (1) supra:

(d) Nitration

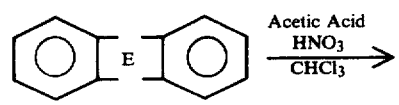

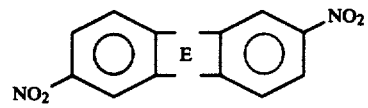

The product obtained was a mixture of cis-trans isomers, of which the trans was isolated for further processing by standard techniques.

(e) Standard Reduction

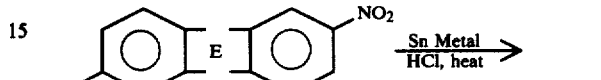

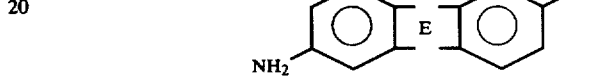

(f) Standard Diazotization

(g) Standard Coupling

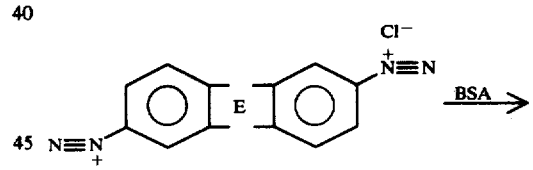

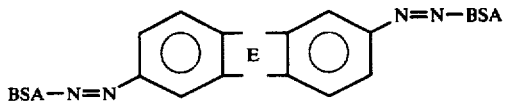

In further explanation, the diazo coupling of (g) actually takes place at tyrosine (amino acid) residues existing on the BSA molecule. Thus, the coupling takes place as follows:

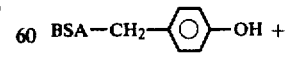

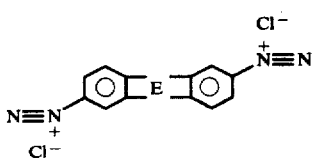

-continued

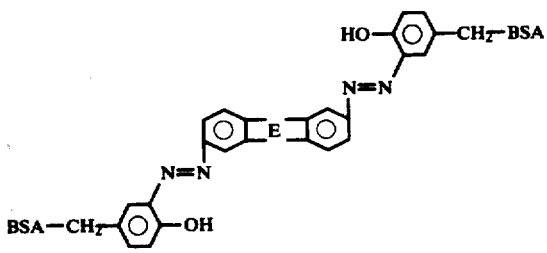

(C) Preparation of the Membranes (1) The dinitrophenyl-containing membrane was prepared by weighing 1.0 mg of the DNP-DB-18-C-6 carrier-conjugate which was the product of (B) (1) (c) supra into a 6 ml vial. 0.25 g of powdered polyvinyl chloride (PVC) was added along with 0.25 ml of dibutyl sebacate (DBS), after which 5.0 ml of tetrahydrofuran (THF) was added and the mixture stirred until a solution resulted.

This solution was poured into a 48 mm dia. petri dish (15 mm deep) and was partially covered with a watch glass to allow the slow evaporation of the solvent THF.

Upon drying, a transparent flexible membrane 11, FIG. 1, about 0.2–0.3 mm thick was obtained, which was stored at room temperature in the dry state.

(2) The BSA-containing membrane was prepared by weighing 50.0 mg of the BSA-DB-18-C-6 carrier-conjugate of (B) (2) (g) supra, first powdered and sieved through a 105 micron mesh screen, into a 6 ml via. 0.25 g of triacetyl cellulose and 0.35 ml of p-nitroethyl benzene were added. A mixture of 5.0 ml methylene chloride and ethanol, in 9:1 v:v proportion, was added to dissolve the cellulose. The BSA-DB-18-C-6 was not dissolved in the solution but was suspended throughout.

The membrane was formed as described for the dinitrophenyl case of (C) (1) supra.

(D) Operation

The active component of the electrode of this invention is the cation complexing crown ether, DB-18-C-6. The crown ether, when placed in the membrane, imparts cation response and selectivity to the membrane. Thus, the DB-18-C-6 containing membrane will respond, selectively, to Group IA and Group IIA cations. The ions which yield higher electrode potential responses are said to be more selective than those giving lower potentials, operation being a function of the equilibrium association constants of DB-18-C-6 with each specific cation. The order of selectivity has been determined to be $K^+ > Na^+ > Ca^{+2} > Mg^{+2}$.

In order to stabilize the ionic strengths of the highly selective $K^+$ and $Na^+$ ions employed in antibody determinations according to this invention, predetermined amounts of $CaCl_2$ (or the less selective, and consequently less preferred, $MgCl_2$) are added to the samples, which complicates the electrode responses obtained.

It is believed that the potential relationships responsible for operation are as follows, it being understood that theory is not fully substantiated by practice at the present time.

$$E = E^o + \frac{RT}{F} \ln [a_i + K_{ij}^{Pot} a_j^{\frac{1}{z}}] \text{ wherein}$$

E = the electrode potential measured, p $E^o$ = a constant consisting of the sum of several nonchanging potentials in the system, RT/F is the quotient of the gas constant times absolute temperature divided by Faraday's constant, $a_i$ is the activity of the cation preselected as the primary cation (i.e., $K^+$ or $Na^+$).

$K_{ij}^{Pot}$ is the potentiometric selectivity constant, which relates the selectivity of cation (i) over cation (j), that is, $K^+$ or $Na^+$ over $Ca^{+2}$ or $Mg^{+2}$, and d $a_j^{\frac{1}{z}}$ is the activity of the secondary, or interfering cation, which is raised to the reciprocal of its charge, i.e., ½ for either $Ca^{+2}$ or $Mg^{+2}$.

It is known that the potentiometric selectivity constant, $K_{ij}^{Pot}$, is approximately equal to the ratio of the two individual equilibrium association constants for the two different ions involved, i.e.:

$$K_{ij}^{Pot} \approx \frac{K_{as,j}}{K_{as,i}}$$

The constant $K_{ij}^{Pot}$ can be determined experimentally. Specifically, applicants measured the $K_{ij}^{Pot}$ for a sample solution containing, typically, $1.0 \times 10^{-3}$ M KCl and $5.1 \times 10^{-2}$ M $CaCl_2$. These concentrations were empirically determined to yield the greatest response to the antibody involved, in this instance the DNP group.

Once the $$K_{K^+,Ca^{+2}}^{Pot}$$

was determined, the specific DNP group antibody was added, which thereupon interacted with the membrane to produce a quantitative potential change. Then $$K_{K^+,Ca^{+2}}^{Pot}$$

was remeasured after the antibody had interacted with the membrane, whereupon it was found that the remeasured value was numerically greater than the first measurement.

From the foregoing, it is clear that the factors E', RT/F, $a_{K^+}$ and $a_{Ca}^{\frac{1}{2}}+2$ remain constant, whereas $$K_{K^+,Ca^{+2}}^{Pot}$$

increases in a positive sense as a result of antibody addition. It is therefore concluded that the electrode responds quantitatively when the antibody binds to the hapten, which is coupled to the crown ether, DB-18-6. It is postulated that the antibody bonding changes either, or both, of the equilibrium association constants, $K_{as,i}$ or $K_{as,j}$ thereby changing the selectivity constant $k_{ij}^{Pot}$, resulting in a characteristic value of measured potential E as a function of antibody concentration.

It is stressed that the theory advanced supra is only applicants' best understanding of the underlying phenomena at this time, and is, of course, subject to revision depending upon future research in progress.

At the outset, it will be understood that animal serum contains, typically, 1800 μg/ml of antibodies whereas the analytical curves obtained by this invention cover ranges of, typically, 2–140 μg/ml, thereby necessitating dilution of the as-received samples by a factor of approximately 80 to 900, depending on the concentration of antibodies involved and the specific electrode employed. This dilution was effected by addition of dilute electrolyte to the serum sample in order to simultaneously obtain the essential ionic strength of sample as hereinafter described.

In order to achieve the necessary binding of antigen (or hapten) to antibodies, an ionic strength of about 0.154 M must be maintained in the samples in analysis. Since as-received serum samples contain, typically, $Na=140$ mM, $K=4$ mM, $Ca=5$ mM and $Mg=2$ mM, sufficient amounts of ionizable salts must be added to the diluted samples to bring the strengths to the 0.154 M ionic level. We have found that our analyses can be conducted by the sensing of electropotentials developed by $K^+$, $Na^+$, $Ca^{+2}$ and $Mg^{+2}$ cations, $K^+$ and $Na^+$ giving largest potential change as a function of antibody concentraton in the sample whereas $Ca^{+2}$ and $Mg^{+2}$ give smaller, but still usable, potential responses. Thus, $K^+$ and $Na^+$ cations are preferred because of their higher sensitivities.

In order to simplify collateral investigation of the mechanism of analysis, the Examples hereinafter reported utilized $K^+$ cation exclusively in Example 1 and $Na^+$ exclusively in Example 2, with ionic strengths adjusted in both cases by $Ca^{+2}$ added as $CaCl_2$ in dilute aqueous solution to simultaneously achieve the necessary sample dilutions. However, since the ion carrier DB-18-C-6 hereinbefore described is broadly effective with any ion, a variety of ionic mixtures can be used in the practice of this invention, always within the reasonable bounds of sensitivity as hereinbefore referred to.

Adjustment of ionic strengths and species is conveniently achieved by dialysis equilibrations. Using this technique, the serum sample of Example 1 was adjusted to 1 mM $K^+$ and 51 mM $Ca^{+2}$, whereas $Na^+$ and $Mg^{+2}$ were reduced effectively to zero. Similarly, the serum sample of Example 2 was adjusted to 42 mM $Na^+$ and 17 mM $Ca^{+2}$, whereas $K^+$ and $Mg^{+2}$ were reduced effectively to zero.

As in usual analytical practice, the electrodes of this invention are calibrated against serum samples containing known concentrations of specific antibodies to be analyzed.

The following are examples of operation according to this invention. All potentiometric measurements were made at 30° C. referred to a single-junction reference electrode, specifically an Orion 90-01. Because DB-18-C-6 is a cation carrier, all sample solutions were prepared to contain fixed amounts of either $K^+$, in the case of Example 1, or $Na^+$ in the case of Example 2, with the ionic strength adjusted to 0.154 M with $CaCl_2$ solution. This ensured that the observed potentiometric effects result from immunochemical reactions exclusively and are not caused by changes in ion activities, pH or ionic strength.

EXAMPLE 1

Figure 2:
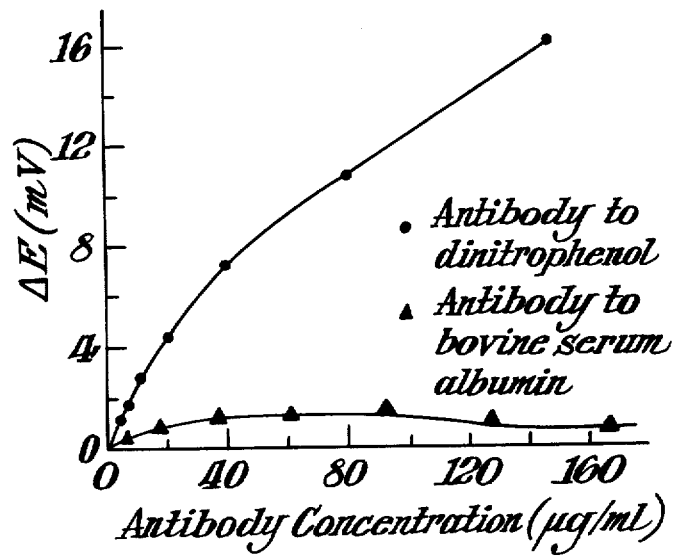

Referring to FIG. 2, evaluating DNP antibody response, a tris-HCl buffer consisting of 0.10 M aqueous solution, pH 7.5 was employed with the membrane of (C) (1) supra.

The upper curve shows a good potentiometric response to DNP antibody.

It is practicable to utilize the antibody to BSA as a blank in this instance, plotted as the lower curve, because the antiserum (i.e., blood serum containing antibodies) to DNP was produced by means of a DNP-BSA conjugate. It is clear that only negligible interference exists from this source.

EXAMPLE 2

Figure 3:
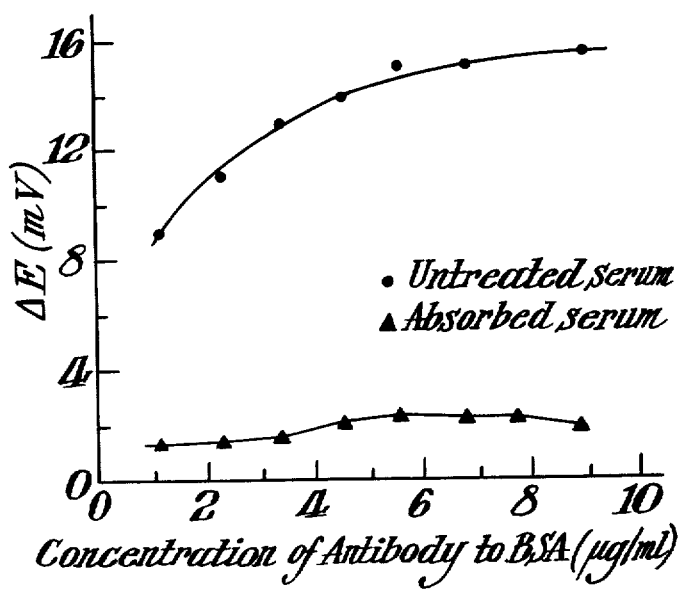

Referring to FIG. 3, evaluating BSA antibody response, a sodium phosphate buffer consisting of a mixture of 0.05 M aqueous solutions of $Na_2HPO_4$ and $NaH_2PO_4$ giving a pH of 7.2 was employed with the membrane of (C) (2) supra.

The upper curve shows a good potentiometric response to BSA antibody.

To prepare an appropriate blank sample, the antiserum to BSA was treated with immobilized BSA to remove the antibody to BSA, as taught by T. Ternyck and S. Avrameas in Scand. J. Immunology (Suppl. 3) (1976) p. 29. As shown by the lower curve, the electrode response to "absorbed" antiserum shows a significant decrease in the magnitude of potential changes.

It should be mentioned that the antiserums employed in Examples 1 and 2 were in media of whole serums marketed by Miles Laboratories and thus contained full spectra of serum proteins, which, however, did not cause interference problems.

By way of evaluating the contribution of the hapten and BSA antigen specifically, measurements were also carried out with the identical membranes employed in Examples 1 and 2, utilizing only the unconjugated ion carriers to confirm whether the potential responses were generated by simple protein absorption on the membranes. These additional experiments yielded electrode potentials near the baseline, indicating that the potential changes obtained with the complete immunoelectrode are the result of interactions of the conjugate with its specific antibody.

Further experiments were performed with the DNP electrode of Experiment 1 by adding dinitroaniline, which mimics the coupled DNP, to the test solution. The antiserum to DNP was then added and no potential changes were observed, because the antibodies were immediately bound by the dinitroaniline molecules, leaving none free to react with the coupled hapten. It is deduced from this that the reaction at the electrode is of the antigen-antibody type.

Potential readings taken over a range of concentrations of antibody to DNP from 2.8 to 145.1 $\mu g/ml$ yielded a standard deviation of 4.1%, with individual potential readings reproducible to $\pm 0.2$ mV. The anti-DNP electrode retained its effectiveness for at least 2 months, and the observed potential changes were fully reversible.

The anti-BSA electrode measured concentrations of antibody to BSA between 1.1 and 8.8 $\mu g/ml$ with a standard deviation of 4.3%, and potential readings were reproducible to $\pm 0.6$ mV.

Both the DNP and BSA electrodes required from 6 to 16 minutes to reach steady-state potentials after the addition of antibody samples.

From the foregoing, it will be understood that the electrodes of this invention can be used to measure antibody levels in body fluids. The hapten dinitrophenyl and its antibody has been studied as a model system, constituting a preliminary basis for the anti-BSA electrode, which latter shows the feasibility of extending the principles to yet other antigen-antibody systems when the antigen can be coupled with a membrane carrier.

What is claimed is:

1. In an antibody-selective membrane electrode useful for the detection of an antibody specific for a preselected hapten or antigen, said membrane electrode having a water-insoluble membrane for separating a test electrolyte from an internal electrolyte, the improvement comprising using as the separating membrane a plasticized water-insoluble solid organic polymer having dispersed therein a cation-selective crown-ether to which the hapten or antigen is covalently bound, wherein said antibody is capable of binding to said antigen or said hapten thereby producing a change in the cation selectivity of said membrane.

2. The electrode of claim 1 in which the crown-ether is a dibenzo-18-crown-6 ether.

3. The electrode of claim 1 in which the hapten is a dinitrophenyl group.

4. The electrode of claim 1 in which the antigen is bovine serum albumin.

5. The electrode of claim 1 in which the polymeric component of the membrane is selected from the group consisting of polyvinyl chloride and triacetyl cellulose.

6. The electrode of claim 5 in which the solid organic polymer is polyvinyl chloride plasticized with an alkyl sebacate.

7. The electrode of claim 6 in which the solid organic polymer is polyvinyl chloride plasticized with dibutyl sebacate.

8. The electrode of claim 5 in which the solid organic polymer is triacetyl cellulose plasticized with p-nitroethyl benzene.

* * * * *